(12) United States Patent
Yamashita

(10) Patent No.: US 7,742,879 B2
(45) Date of Patent: Jun. 22, 2010

(54) METHOD AND APPARATUS FOR CHROMATOGRAPHY MASS SPECTROMETRY

(75) Inventor: Hiromichi Yamashita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 132 days.

(21) Appl. No.: 12/078,241

(22) Filed: Mar. 28, 2008

(65) Prior Publication Data

US 2008/0237457 A1 Oct. 2, 2008

(30) Foreign Application Priority Data

Mar. 30, 2007 (JP) ............... 2007-090058

(51) Int. Cl.
*C12Q 1/68* (2006.01)
(52) U.S. Cl. ............................. 702/20; 702/2
(58) Field of Classification Search ......... 702/2, 702/5, 19, 20, 30; 435/4, 6; 250/281, 282
See application file for complete search history.

(56) References Cited

U.S. PATENT DOCUMENTS 7,473,892 B2 * 1/2009 Sano et al. ............... 250/281

FOREIGN PATENT DOCUMENTS

| JP | 10-282060 | 10/1998 |
| JP | 2000-171450 | 6/2000 |
| JP | 2003-270205 | 9/2003 |
| WO | WO 2004/090526 A1 | 10/2004 |
| WO | WO 2005/079261 A2 | 9/2005 |
| WO | WO 2006/077160 A1 | 7/2006 |

OTHER PUBLICATIONS

Ono, M., et al., "Label-free quantitative proteomics using large peptide data sets generated by nano-flow liquid chromatography and mass spectrometry," MCP Papers in Press, Mar. 21, 2006, p. 1-24, fig. 1-4, Manuscript T500039-MCP200, The American Society for Biochemistry and Molecular Biology, Inc.
Japanese Office Action issued in Japanese Patent Application No. JP 2007-090058 dated Jul. 21, 2009.
Japanese Notice of Rejection issued in Japanese Patent Application No. JP 2007-090058 dated Nov. 24, 2009.

* cited by examiner

*Primary Examiner*—Kiet T Nguyen
(74) *Attorney, Agent, or Firm*—McDermott Will & Emery LLP

(57) ABSTRACT

The results of mass spectrometry are compared; correspondences are established between individual components contained in different samples; the results of establishment of correspondences are checked; and varying components are extracted. At least two samples are compared with respect to the ion intensity corresponding to retention times and mass-to-charge ratios obtained by chromatography-mass spectrometry on the samples having a plurality of components. In ion groups observed as mass spectra, a correspondence between the retention times at which the same component is supposed to be observed is established by determining coincidence between the mass-to-charge ratios and determining that the ion intensity fall within a designated variation.

21 Claims, 11 Drawing Sheets

|  | $T'_2$ | $T'_4$ | $T'_6$ | $T'_8$ | $T'_{10}$ | $T'_{12}$ |
|---|---|---|---|---|---|---|
| $T_1$ |  | ○ |  |  | × | × |
| $T_3$ | ○※ |  |  |  |  | × |
| $T_5$ |  |  | ○※ |  |  |  |
| $T_8$ |  | ○ |  | ○ | ○ |  |
| $T_{10}$ | × |  |  |  |  | ○※ |

FIG. 15

| No. | Computation type | Reference sample | Sample to be corrected | Computed value | Display color | | |
|---|---|---|---|---|---|---|---|
| | | | | | Red | Green | Blue |
| 1 | Difference | 500 | 100 | -400 | 400 | 0 | 0 |
| 2 | Difference | 100 | 500 | +400 | 0 | 400 | 0 |
| 3 | Ratio | 400 | 200 | -2 | 2 | 0 | 0 |
| 4 | Ratio | 200 | 400 | +2 | 0 | 2 | 0 |
| 5 | Both | 700 | 200 | — | 700 | 200 | 0 |
| 6 | Both | 500 | 1000 | — | 500 | 1000 | 0 |
| 7 | Lone | 200 | 0 | — | 200 | 0 | 0 |
| 8 | Lone | 0 | 400 | — | 0 | 400 | 0 |
| 9 | Lone | 500 | 800 | — | 0 | 0 | 0 |
| 10 | Merge | 300 | 700 | — | 700 | 0 | 0 |
| 11 | Merge | 600 | 200 | — | 600 | 0 | 0 |

FIG. 16A

| No. | Retention time of reference sample | Mass-to-charge ratio of reference sample | Retention time of sample to be corrected | Mass-to-charge ratio of sample to be corrected |
|---|---|---|---|---|
| 1 | 3.54 | 325.032 | 3.73 | 325.035 |
| 2 | 7.93 | 401.041 | 8.02 | 401.038 |
| 3 | 12.90 | 659.268 | 12.99 | 659.271 |
| 4 | 15.21 | 518.149 | 15.17 | 518.150 |
| 5 | 17.42 | 740.193 | 17.40 | 740.192 |

FIG. 16B

| No. | Retention time of reference sample | Mass-to-charge ratio of eference sample | Computation result (Ratio) |
|---|---|---|---|
| 1 | 14.36 | 790.453 | 243.56 |
| 2 | 31.07 | 610.460 | 219.91 |
| 3 | 24.90 | 531.879 | 186.02 |
| 4 | 10.49 | 493.071 | 171.30 |
| 5 | 19.11 | 959.723 | 160.79 |

FIG. 16C

| No. | Retention time of reference sample | Mass-to-charge ratio of reference sample | Identification result |
|---|---|---|---|
| 1 | 11.34 | 780.443 | Protein A - Seq A1-DescriptionA |
| 2 | 42.97 | 909.460 | Protein B - Seq B1-DescriptionB |
| 3 | 37.90 | 534.879 | Protein C - Seq C1-DescriptionC |
| 4 | 40.42 | 893.051 | Protein A - Seq A2-DescriptionA |
| 5 | 29.13 | 869.723 | Protein C - Seq C2-DescriptionC |

METHOD AND APPARATUS FOR CHROMATOGRAPHY MASS SPECTROMETRY

CLAIM OF PRIORITY

The present application claims priority from Japanese application JP 2007-90058 filed on Mar. 30, 2007, the content of which is hereby incorporated by reference into this application.

BACKGROUND OF THE INVENTION

1. Field of the Invention

The present invention relates to a method and apparatus for chromatography mass spectrometry.

2. Background Art

When a sample constituted by a plurality of components is measured by a liquid chromatography-mass spectrometry using a combination of a separating instrument and a mass spectrometer, the sample components are successively observed as ions. By this liquid chromatography-mass spectrometry, a three-dimensional data in which mass spectra consisting of the ion intensity with respect to the mass-to-charge ratio are accumulated at certain times (so-called retention times) can be obtained. Trials have been made by using such data for quantitative comparative analysis of components contained in different samples. In many cases, however, the retention times of individual components are not reproduced. There is a demand for a method of establishing correspondences between identical components between samples.

Methods for correcting retention times so that identical components have the same retention times have been devised on the assumption that even if the retention times of components vary, the order in which the components are observed is not changed. For example, patent document 1 and a non-patent document 1 disclose methods of establishing correspondences between retention times by considering the fact that similar mass spectra are produced from components identical to each other. In the methods disclosed in patent document 1 and a non-patent document 1, similarity between samples are computed with respect to mass spectra obtained by measuring the samples. However, when individual sample components vary under circumstances where the separating effect of chromatography is not sufficiently high and where ions derived from a plurality of components are observed in mass spectra, the mass spectra do not necessarily coincide with each other with accuracy. Dynamic programming is then used to successively obtain the correspondence relationships between retention times through observation of sample components.

[Patent document 1] WO 2004/090526 A1

[Non-patent document 1] Masaya Ono, Miki Shiashige, Kazufumi Honda, Tomohiro Isobe, Hideya Kuwabara, Hirotaka Matsuzuki, Setsuo, Hirohashi, and Tesshi Yamada "Label-free Quantitative Proteomics Using Large Peptide Data Sets Generated by Nanoflow Liquid Chromatography and Mass Spectrometry" Mol. Cell. Proteomics, 5: 1338-1347 (2006).

SUMMARY OF THE INVENTION

The present invention relates to a technique for making quantitative comparison between individual components in different samples by using the results of chromatography-mass spectrometry on a sample such as plasma containing many kinds of components. In measurement results obtained by chromatography-mass spectrometry, individual components are observed as amounts of ions characterized by retention times and mass-to-charge ratios. In the results of measurement of different samples, however, retention times do not always coincide with each other with respect to identical components. It is, therefore, difficult to establish correspondences between identical components between samples. Also, for establishment of correspondences between components, a method of easily checking the correspondences is important.

The conventional methods require obtaining in advance similarity of mass spectra probable to have correspondences of retention times between samples and, hence, an increased amount of computation. Further, in a case where the time intervals at which mass spectra are obtained are coarse, and where mass spectra themselves, from which correspondences between retention times are to be successively determined, do not exist, there is a possibility of the accuracy of establishment of correspondences being reduced. Non-patent document 1 describes use of a method of arranging, in correspondence with different samples, displays indicating the retention time and mass-to-charge ratio on coordinate axes and indicating the ion intensity by shades, but presents no means for efficiently checking the correspondence relationship by observing individual components.

An object of the present invention is to provide a method or apparatus for enabling, in a simpler computation processing environment, establishment of correspondences between individual components containing in different samples, a method or apparatus of efficiently checking the results of establishment of correspondences, or a method or apparatus for extracting varying components.

According to the present invention, at least two samples are compared with respect to the ion intensity corresponding to retention times and mass-to-charge ratios obtained by performing chromatography-mass spectrometry on a sample containing a plurality of components; ion groups are thereby observed as mass spectra; and a correspondence is established in the ion groups between the retention times at which the same component is observed, by determining coincidence between the mass-to-charge ratios and determining that the ion intensity fall within a designated variation.

Also, in the results of chromatography-mass spectrometry on at least to samples, a map display indicating the ion intensity by colors or shades on the coordinate axes representing the retention time and the mass-to-charge ratio and a display of a mass chromatogram of components to be observed or a chromatogram formed of the maximums of individual mass spectra are produced by setting a common axis for the retention time and by connecting, by line segments, the retention times at which components correspond to each other. Also, with respect to the retention times and the mass-to-charge ratios corresponding to each other between different samples, values of differences or ratios in ion intensity, ion intensities existing in only one of the two samples or the ion intensities of the two samples are indicated as a gray-level map by being color-coded according to the values or the samples from which the ion intensities are derived. Further, the individual components are displayed on a map by being converted into their representative points to enable comparative analysis. Also, a map, a mass spectrum and a chromatogram formed by enlarging a region in the vicinity of the corresponding retention time and mass-to-charge ratio, characteristics of an observed ion, the result of identification and other sorts of information are displayed by designating a position and selecting the component with a mouse.

According to the present invention, establishment of correspondences between individual components containing in different samples can be executed in a simple computation processing environment, and the results of establishment of correspondences can be efficiently checked. Also, components varying between different samples can be extracted with efficiency.

BRIEF DESCRIPTION OF THE DRAWINGS

FIG. 15 is a diagram showing an example of computed values and display colors with respect to computation types; and FIG. 16 is a diagram showing an example of a list having position information.

DETAILED DESCRIPTION OF THE PREFERRED EMBODIMENTS

There are a great number of cases of comparing the components of samples each having a mixture of a multiplicity of components, e.g., cancerous and non-cancerous tissues, blood or urine before and after giving a dose or an operation, a gene-disrupted strain and a wild strain, and individual-derived tissues differing in phenotype. For example, various approaches to such cases, including a trial to find a component observable only at an initial stage of a particular disease by extracting blood or urine from an able-bodied person and a patient and comparing the components thereof and to use the finding of the component for diagnosis, and verification of a causal relation between a particular component and a state of a disease after recuperation for devising a treatment plan, are being made.

The present invention enables quantitative comparison between individual components in samples of the same kind derived from living bodies, e.g., serum, plasma, urine, extracted tissues and cultivated cells such as yeast each having a mixture of a multiplicity of components. In particular, in a process of listing and successively checking components varying largely, the present invention facilitates a process for verification as to erroneous determination and a result of identification of a mass spectrum.

If a component which has exhibited a variation can be identified, it becomes a marker candidate indicating a difference between samples and has a significance as a subject of further study. Further, this effect is considered to lead directly to a study of a variation on the gene or protein level, a study of differences between metabolic pathways and to contribute to basic comparative experiments in the field of medical science and biochemistry.

The present invention will be described in detail with reference to the accompanying drawings.

1. Sample Characteristics

The present invention is for obtaining quantitative knowledge by establishing correspondences of individual components between samples of the same kind having a plurality of components, and uses characteristics in terms of kind and amount of existence of components contained in samples of the same kind. That is, many components common to samples of the same kind can be observed, and the fact that quantitative variations among samples fall within a certain range with respect to a great majority of the components is utilized.

In a case where there are not many components common to samples to be compared, the present invention is applied in such a manner that a sample obtained by mixing the samples to be compared is set as a reference sample, and each of the samples before mixing is set as a sample to be corrected. That is, all the components contained in the samples to be corrected are contained in the reference sample and, therefore, a large number of common components can be observed. Application of the present invention is thus made possible.

Figure 1:
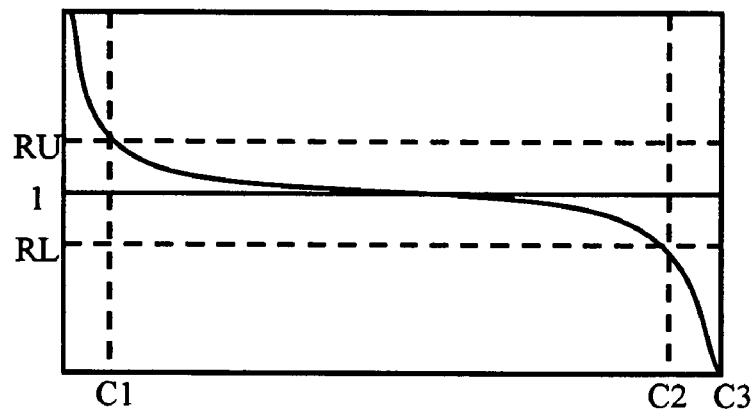
FIG. 1 is a model diagram in which amount ratios are arranged in descending order on a component-by-component basis between samples.

FIG. 1 is a graph of the existence ratio of components contained in samples assumed as a reference sample and a sample to be compared. The ordinate corresponds to a logarithmic scale for indicating the existence ratio of each component, and the abscissa corresponds to ordinal numbers for an arrangement of the components such that the existence ratio is in descending order. Accordingly, the component having the highest increasing rate is positioned at the left end of the graph, while the component having the highest decreasing rate is positioned at the right end. In this graph, the C1-th to C2-th components are contained in the range between the existence ratios RU and RL. C3 is the total number of components contained in the samples. Then, in this case, the majority of the components are within the range defined by the limited existence ratio.

2. Measuring Apparatus

Figure 2:
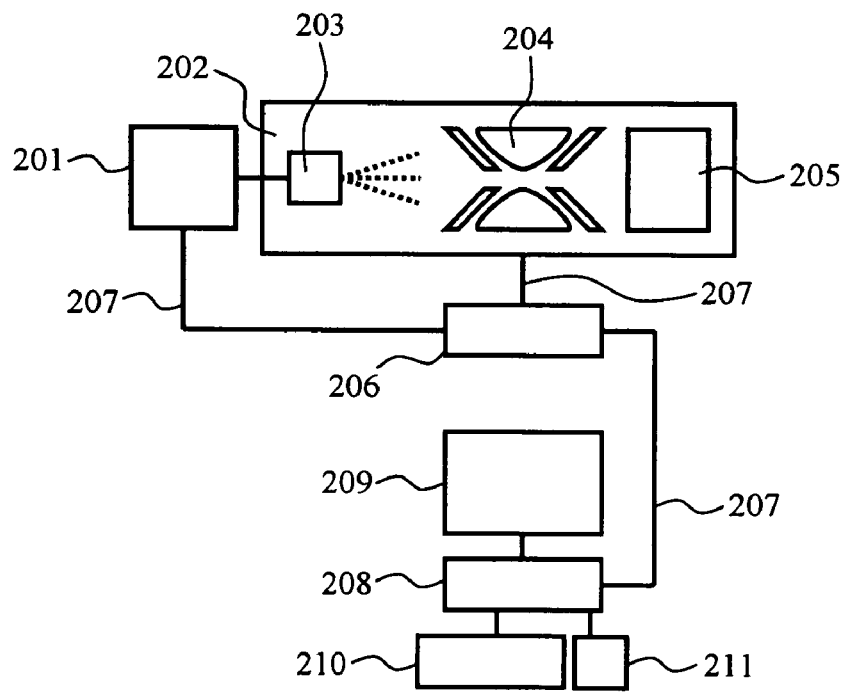
FIG. 2 is a diagram showing an example of a mass spectrometry apparatus according to the present invention.

FIG. 2 is a schematic diagram showing an example of the configuration of a chromatography mass spectrometer according to the present invention.

Sample components separated by a liquid chromatograph 201 are introduced into a mass spectrometer main unit 202 to be moved to an ion source 203, to a mass filter 204 and to a detector 205. Further, the sample components can be successively collected as a mass spectra in a data processor 208 via a controller 206. These devices and instruments are connected via signal lines to be used for control and collection of information. The data processor has a display 209, a keyboard 210 and a mouse 211. While an ion trap type of mass filter is illustrated in the figure, a device using a magnetic field, a quadrupole mass filter or the like may alternatively be used if it is capable of obtaining a mass spectra derived from sample components in a time series.

In this configuration, a mass spectra formed by the ion intensity with respect to the mass-to-charge ratio are continuously obtained in synchronization of a start of separation of sample components by the liquid chromatograph. Further, the mass spectra are accumulated at each of retention times at which they are observed.

As a method for ionization, a method (soft ionization method) arranged to minimize damage to sample components, typified by an electrospray ionization (ESI) is preferred. In a case where a separating unit and a chromatography mass spectrometer are connected to each other and where such an ionization method is adopted, the probability that the results of measurement of samples each constituted by a plurality of components directly reflect the individual sample components is high. That is, ideally, the mass spectra successively measured clearly reflect the qualitative and quantitative differences between the individual sample components.

In some cases of ionization by ESI or the like, ions of one component having different charges (so-called multiply-charged ions) are produced. Also, a plurality of ions are often observed in the neighborhood due to the influence of a stable isotope. No mention will be made of these unless necessary. Description will be made in this specification by assuming that components and ions correspond to each other. Also, the present invention can be applied to a combination of a gas chromatograph and chemical ionization or the like in the way of limiting damage to components.

Some mass spectrometers can obtain a mass spectrum (so-called MSMS spectrum) after performing a process in which produced ions are activated, for example, by being caused to impinge against gas molecules, and bonds in ion molecules are thereby fragmented to produce smaller ions. Since this MSMS spectrum is produced by fragmenting component ions, information relating to the structure of the component ions for example can be obtained. In the description below, a mass spectrum in which component ions are observed is referred to as "MS spectrum" if there is a need to explicitly denote it in contrast with an MSMS spectrum. An ion fragmented to obtain an MSMS spectrum is called a precursor ion.

Further, in some cases, a precursor ion may be selected from an obtained MS spectrum to enable real-time measurement of a corresponding MSMS spectrum. In some of such cases, MS and MSMS spectra mixing with each other can be discriminated from each other and qualitative information on components can be obtained from the MSMS spectrum. Also, with respect to MS spectra obtained at a retention time, quantitative knowledge can be obtained from information about a precursor ion contained in the MS spectra measured at a vicinal retention time.

In the present invention, a candidate for correcting a retention time is discretely set. The present invention can therefore be adapted to measurement including measurement of MSMS spectra, i.e., a case where MS spectra are obtained at coarse intervals.

3. Method of Establishing Correspondences Between Components

For establishment of correspondences of components between different samples of the same kind, groups of three-dimensional data on the ion intensity with respect to the retention time and the mass-to-charge ratio are compared. The mass-to-charge ratio is a specific value derived from the element composition of a component molecule. In general, the reproducibility of the mass-to-charge ratio is high and the mass-to-charge ratio is effective in discriminating components. The retention time depends largely on an environment at the time of separation and its reproducibility is comparatively low. According to the present invention, establishment of the correspondences between components with respect to discretely-set retention times is required.

Figure 3:
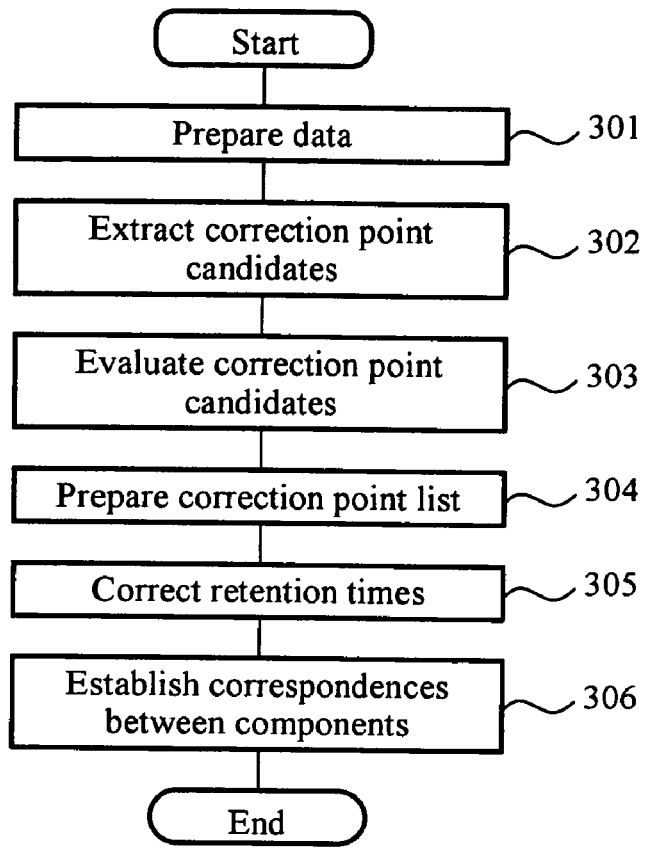
FIG. 3 is a diagram for explaining the flow of basic processing in the present invention.

FIG. 3 shows the flow of basic processing. Data used in processing is first prepared from measurement results corresponding to samples to be compared (301). Subsequently, retention times probable to correspond to each other are discretely extracted as correction point candidates (302). Mass spectra respectively observed at the correction point candidates are obtained evaluated with respect to and the probability of coincidence between components (303). Further, components to be used for correction of the retention times are obtained to prepare a correction point list (304). Correction of the retention times is thereafter performed (305), the correspondence of each component is established and some of the components that have varied are explicitly shown (306).

According to the present invention, a method of determination based on the characteristics of samples shown in FIG. 1 is applied to evaluation of correction point candidates in step 303. The concept of this method will be described with reference to FIG. 4. In the following description, a case of comparing a reference sample provided as a retention time reference and a sample whose retention time is to be corrected is considered and evaluation of the correspondence between mass spectra derived from the two samples is assumed.

Figure 4:
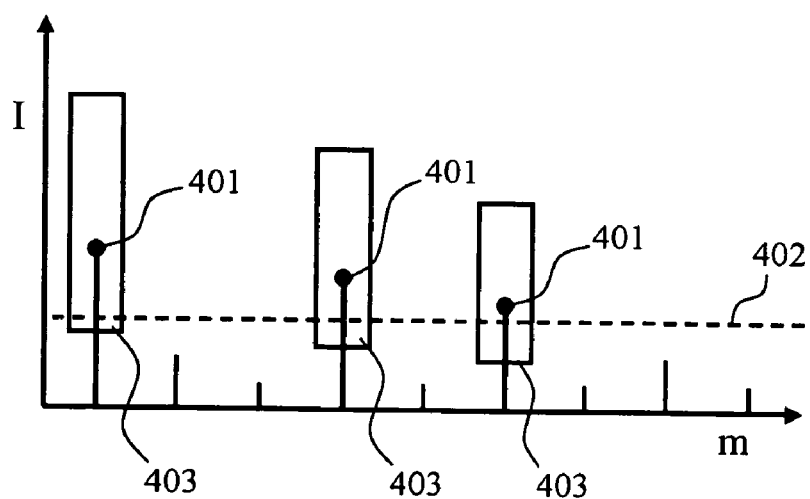
FIG. 4 is a diagram for explaining a method of evaluating correspondences between components.

FIG. 4 shows a mass spectrum derived from a reference sample. A mark • 401 indicates an ion having an intensity equal to or higher than a threshold 402 indicated by the broken line, and a rectangle 403 surrounding the mark • indicates a variation region in the sample to be corrected.

If individual ions constituting the mass spectrum are assumed to reflect components contained in the sample, and if their intensities are assumed to reflect relative amounts, the positions of the upper and lower ends of the rectangles, i.e., the upper and lower limit values of the intensities of the ions, can be defined by using RU and RL shown in FIG. 1, as shown below.

$$\text{Upper limit value}=\text{Ion intensity}\times RU \quad (1)$$

$$\text{Lower limit value}=\text{Ion intensity}\times RL \quad (2)$$

With respect to the mass-to-charge ratio, a constant, a value proportional to the value of the mass-to-charge ratio or the like is assumed to be an error ($\delta m$), and its range is set.

$$\text{Mass-to-charge ratio lower limit}=\text{mass-to-charge ratio}-\delta m \quad (3)$$

$$\text{Mass-to-charge ratio upper limit}=\text{mass-to-charge ratio}+\delta m \quad (4)$$

Similarly, an error ($\delta t$) is also set with respect to the retention time and the retention time is treated by assuming that there is no difference larger than this value.

$$\text{Retention time lower limit}=\text{retention time}-\delta t \quad (5)$$

$$\text{Retention time upper limit}=\text{retention time}+\delta t \quad (6)$$

The range of ions to be observed in the mass spectrum of a sample to be corrected can be set in this way. If all ions observed through the ion intensity equal to or higher than the threshold fall within this range, the related components are regarded as corresponding to each other.

The correspondences between retention times obtained by a method such as described above depend on the probability of events in which a set of ions is observed in common. Accordingly, conditions including a method of selecting ions to be evaluated as a set, a range in which ions are assumed to vary, a lower limit of the number of ions by which coincidence is recognized are assumed as well as the above-described δm and δt. Evaluation such as described above is executed with respect to all combinations of the correction point candidates discretely extracted, thereby determining whether or not the components correspond to each other.

The present invention is effective in a situation where the number of components is large and separation by chromatography is inadequate. That is, components simultaneously observed at a certain retention time are obtained in the mass spectra at the point in time. However, it is conceivable that in a situation where the number of components is comparatively small and the state of separation of components is good, vicinal spectra are added together at each value of the mass-to-charge ratio to obtain mass spectra for evaluation, or vicinal retention times are searched for at each value of the mass-to-charge ratio to obtain at the maximum of the ion intensity mass spectra to be evaluated.

Mass spectra to be evaluated include chemical noise or the like not derived from samples. It is desirable to exclude such ions in advance for the purpose of reducing the influence on processing performed afterward.

In the present example, two samples: a reference sample and a sample to be corrected are compared. The range of application of the present invention can be extended, for example, by applying this concept to three or more samples and using a set of ions having the highest average value of the intensity as a reference. Also, the coincidence of groups of components may be determined by setting as a condition the proportion of observed ions falling within a set range.

4. Means for Checking Establishment of Correspondences Between Components

Means for looking over all data and thereafter checking each component have been devised for the purpose of visually verifying the correctness of establishment of correspondences of components between samples. Description will be made of them with reference to FIGS. 5 and 6.

(1) Large-Region Checking Means

Figure 5A:
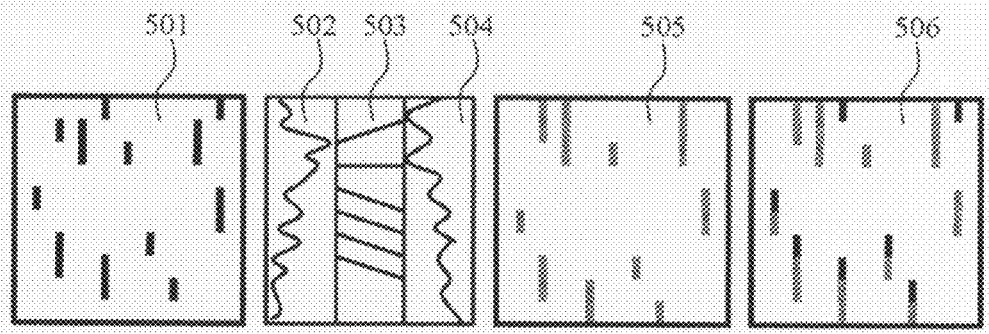
FIG. 5 is a diagram for explaining a method for looking over measurement results, the correspondences between retention times, and the correspondences between components.

FIG. 5A shows the results of measurement of a reference sample and a sample to be corrected before retention time correction, and the correspondence relationships between retention times and components of the samples. In FIG. 5A, reference numeral 501 denotes a map which shows measurement results derived from the reference sample, and in which the ordinate represents retention time, the abscissa represents the mass-to-charge ratio and the corresponding ion intensity is indicated by a color or a gray level. This map and an adjacent chromatogram 502 share the retention time coordinate axis with each other.

Similarly, a chromatogram 504 and a map 505 of the sample to be corrected share the retention time coordinate axis. Further, line segments 503 positioned between the two chromatograms indicate the correspondence relationship between the retention times in the chromatograms and the maps. A state where the line segments 503 are uniform in inclination means that the retention time tends to shift uniformly. The results of the above-described preparation of a correction point list in step 304 shown in FIG. 3 are reflected in the line segments 503.

A comparative analysis map 506 at the right end corresponds to the results of comparison and analysis of the points in the other maps 501 and 505 with respect to the corresponding retention time and mass-to-charge ratio. In this map, characteristic ions can be looked over, for example, through a display of the results of measurement of the two samples in a combined state, a display of the components observed in only one of the samples, and the values of the difference and the ratios of the components.

Figure 5B:
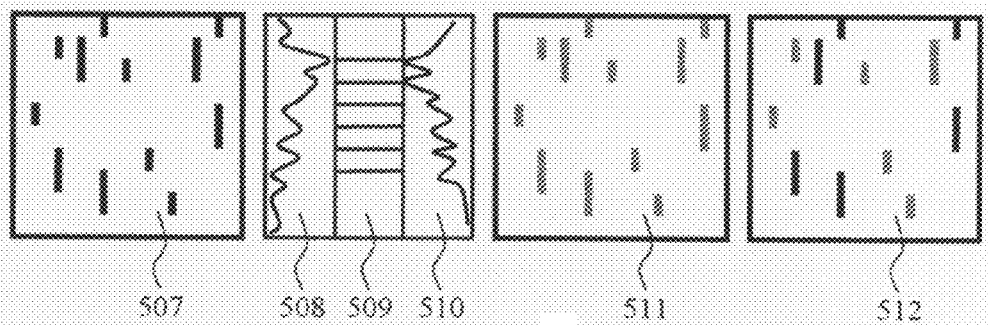

FIG. 5(B) shows a state after correction of the retention times from the state shown in FIG. 5(A). While a map 507 of the results of measurement of the reference sample is identical to the map 501 before correction, a chromatogram 510 and a map 511 of the sample to be corrected are images shifted along the retention time direction because the retention times have been corrected. Further, all line segments 509 indicating the correspondences between the retention times are parallel to each other and indicate that the retention times are the same. A comparative analysis map 512 is also updated in synchronization with correction of the retention times.

Thus, well-balanced examination of the whole can be achieved by looking over the results of comparison and analysis of the data on the results of measurement of the reference sample, the results of measurement of the sample to be corrected and the retention time correspondence relationship.

The comparative analysis maps 506 and 512 serve as an aid in determining the correspondence relationship between components, for example, in such a manner that when the retention times are relatively shifted, the ions derived from the two samples are displayed in a state of being shifted relative to each other. Further, the values of differences or ratios may be obtained and displayed on the maps to emphasize characteristic components and to thereby facilitate narrowing-down of components to be compared.

(2) Local Checking Means

A portion in the above-described maps or one of the line segments indicating the correspondences between the retention times may be directly designated with a mouse to display an enlarged diagram at the corresponding position, thereby enabling more detailed verification of the correspondence relationship. Description will be made of this with reference to FIG. 6.

Figure 6A:
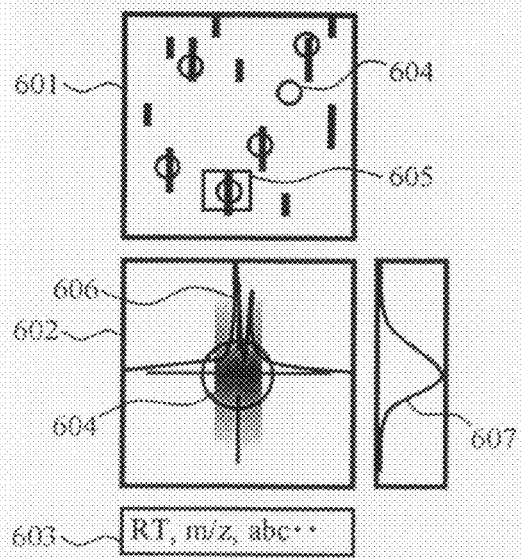
FIG. 6 is a diagram for explaining a method for locally evaluating the correspondences between components.

An upper map 601 in FIG. 6(A) corresponds to the maps in FIGS. 5(A) and 5(B) and enables the whole measurement data to be looked over. A lower map 602 is an enlarged display of a region indicated by a rectangle 605 in the upper map. In an information display area 603 below the lower map 602, the intensity, the retention time, the mass-to-charge ratio, the mass in the case of a single-charge and the charge number of the ion observed at a center of the enlarged region are displayed. A mark ○ 604 indicates a position at which an MSMS spectrum is obtained, a position to which information such as the result of identification of a component corresponds, or the like. The contents of information related to the mark ○ 604 are also displayed in the information display area 603.

A mass spectrum 606 displayed in the map 602 is of a central portion of the enlarged area, and shares the mass-to-charge ratio coordinate axis with the map. A mass chromatogram 607 corresponding to the mass-to-charge ratio of the central portion is also displayed to enable the spectrum and the mass chromatogram to be checked simultaneously with each other.

Figure 6B:
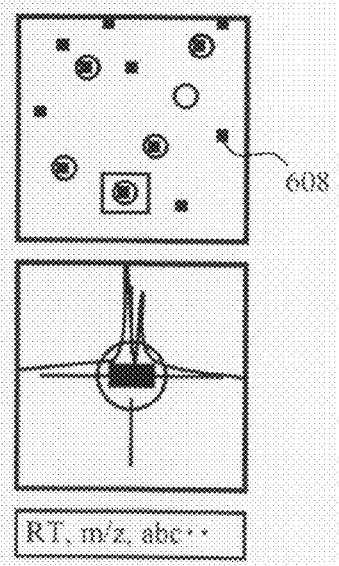

FIG. 6(B) shows an image of extracted representatives of the components from the state shown in FIG. 6(A). This corresponds to the results of the above-described establishment of correspondences on a component-by-component basis. Each component is positioned at one point 608 corresponding to a peak of the mass chromatogram. This point has, for example, a value in terms of its height or volume at the position at which the maximum of the ion intensity in the component is given.

Thus, the displays shown in FIGS. 5(A), 5(B), and 6(A) are changed into displays on a component-by-component basis such as shown in FIG. 6(B) to enable narrowing-down of points at the time of comparison between components.

(3) Operability

There is a need to efficiently identify the target position in the local display shown in FIGS. 6(A) and 6(B). For example, designation of an arbitrary position on a map with a mouse and designation of a list having position information are effective. There are many effective examples of the latter in particular, including a list of retention time correction points, the results of computation of differences or ratios and a list of identification results.

FIG. 16 shows examples of such lists. FIG. 16(A) shows, as an example of a retention time correction point list, the correspondence between retention times and mass-to-charge ratios in a reference sample and a sample to be corrected. FIG. 16(B) shows, as an example of a computation result list, ratio values with respect to retention times and mass-to-charge ratios. FIG. 16(C) shows, as an example of an identification result list, a list of proteins corresponding to retention times and mass-to-charge ratios. A portion of such lists is designated with a mouse or the like to produce a local display of the corresponding position.

In a retention time correction point list, data may be sorted and displayed so that retention times are in ascending order, thereby facilitating checking of correction points in sequence. In a computation result list, data may be sorted and displayed so that values of differences or ratios are in descending or ascending order, thereby facilitating checking of characteristic components. In an identification result list, it is effective to indicate information including names of corresponding proteins, amino acid sequence information and functions relating to the proteins. Also, entries containing particular letters in the list can contribute to checking of proteins of the same name or the same kind.

A user can designate a selection as to whether the local displays are independently produced each in association with one of the large-region maps or an area common to all the maps is displayed by being enlarged. After correction of the retention time, a display common to all the enlarged display may be produced to enable the correspondences between the components to be efficiently checked.

Displays such as those described above enable grasp of the outline of measurement results based on large-region maps and enables evaluation of a component to be observed based on displays of local maps and mass spectra simultaneously with grasp of the outline.

Embodiment 1

An embodiment of the above-described method will be described.

An embodiment described below is an example of a process in which proteins are extracted from a reference sample and a sample to be corrected; liquid chromatography mass spectrometry is executed after enzyme digestion; and the correspondences between individual components is determined from the results of the mass spectrometry.

1. Outline

Figure 7:
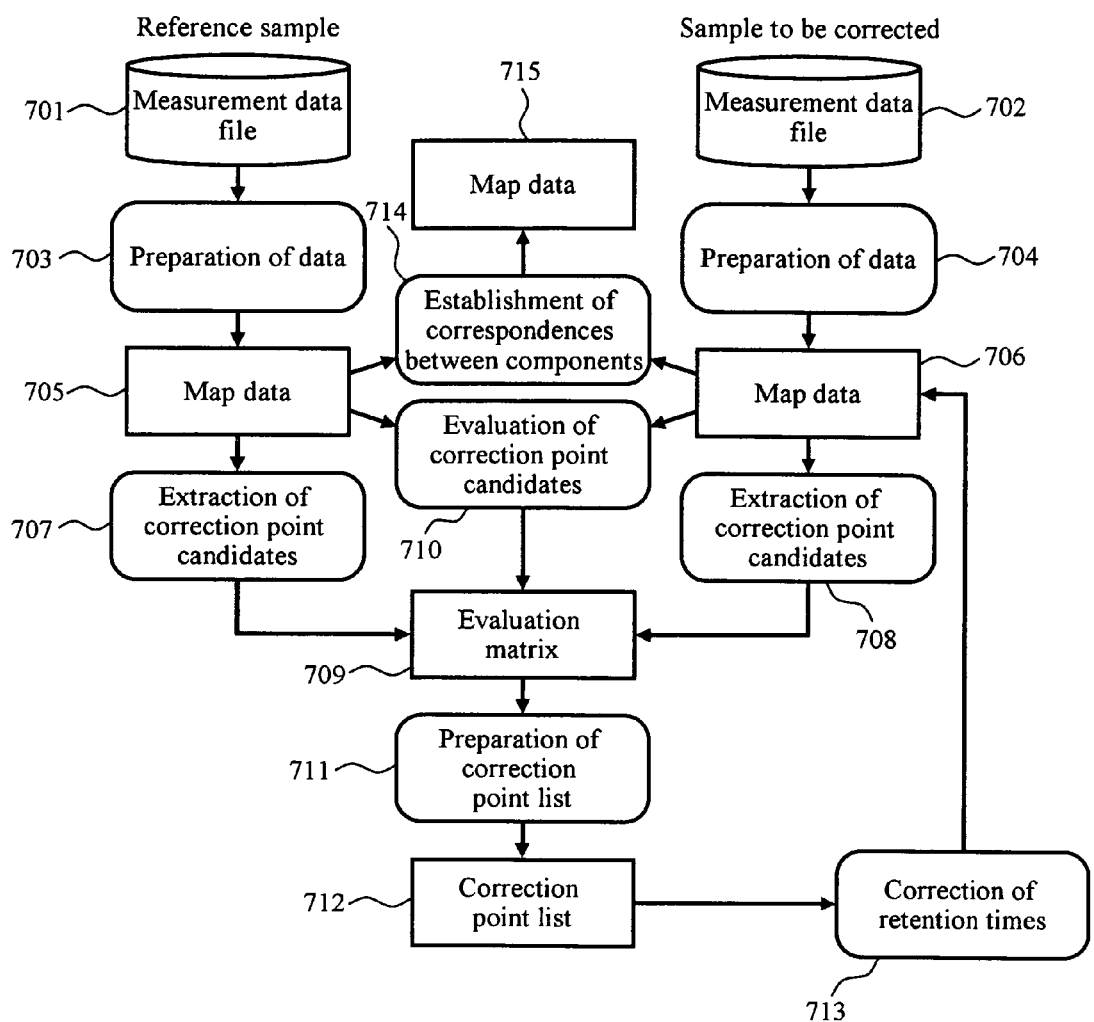
FIG. 7 is a diagram for explaining the relationship between data and processing in the method of the present invention.

A more concrete form of the flow of processing shown in FIG. 3 is given and the relationship between main data and the processing is shown in FIG. 7.

Measurement data files 701 and 702 for a reference sample and a sample to be corrected are first prepared. In the measurement data files, data including MS spectra retention times, mass-to-charge ratios and ion intensities is stored. Data preparation processing (703, 704) is performed to organize these sorts of data and to enable easy access to target mass spectra or particular ions. As a result, map data groups 705 and 706 corresponding to the reference sample and the sample to be corrected are prepared. Details of the map data will be described later with reference to FIG. 11.

To obtain retention time correction points, retention times which become correction point candidates are discretely extracted from the results of measurement of the samples (707, 708). An evaluation matrix 709 in which the obtained candidates are associated with rows and columns is prepared and given contents by evaluation of correction point candidate (710). In this evaluation, the variation range assumed in FIG. 1 is applied and the establishment of correspondences between components is evaluated. Further, processing including elimination of a possibility of pseudo-positivity or the like is performed to complete the evaluation matrix. Details of the evaluation matrix 709 will be described later. Subsequently, processing for accumulating components each corresponding to one of the correction points in a correction point list 712. Components used for correction of the retention times between the different samples are extracted by processing such as described above.

In retention time correction (713), the retention times of the map data 706 of the sample to be corrected are corrected on the basis of the correction point list 712. In this correction, the same retention time is assigned to the components of the reference sample and the sample to be corrected registered in the correction point list 712, and correspondences are established by interpolation between the components. Ideally, the map data 706 on the corrected sample thereby updated coincides in retention time with the map data 705 on the reference sample. However, the map data 706 and the map data 705 differ in data size because the mass spectra were obtained at different times and with different frequencies. These conditions are not suitable for immediate comparison between these groups of data.

In establishment of correspondences on a component-by-component basis (714), the map data groups 705 and 706 from each sample are first converted into representative points on a component-by-component basis such as shown in FIG. 6(B). Further, correspondences between the components are established by checking the individual components of the sample to be corrected against the reference sample, thereby preparing map data 715. This map 715 and the map 705 of the reference sample are equal in size to each other and the retention times and the mass-to-charge ratios thereof can be brought into one-to-one correspondence with each other, thus facilitating quantitative comparison between individual components.

2. Explanation of User Interface 2.1 Basic View

An example of an on-screen display will be described with reference to FIG. 8. The example described below is an example of a viewer which is illustrative of a state before correction of retention times, and which is capable of being adapted to comparative analysis of components with respect to the correspondence relationship between correction points, a state after correction, etc.

Figure 8:
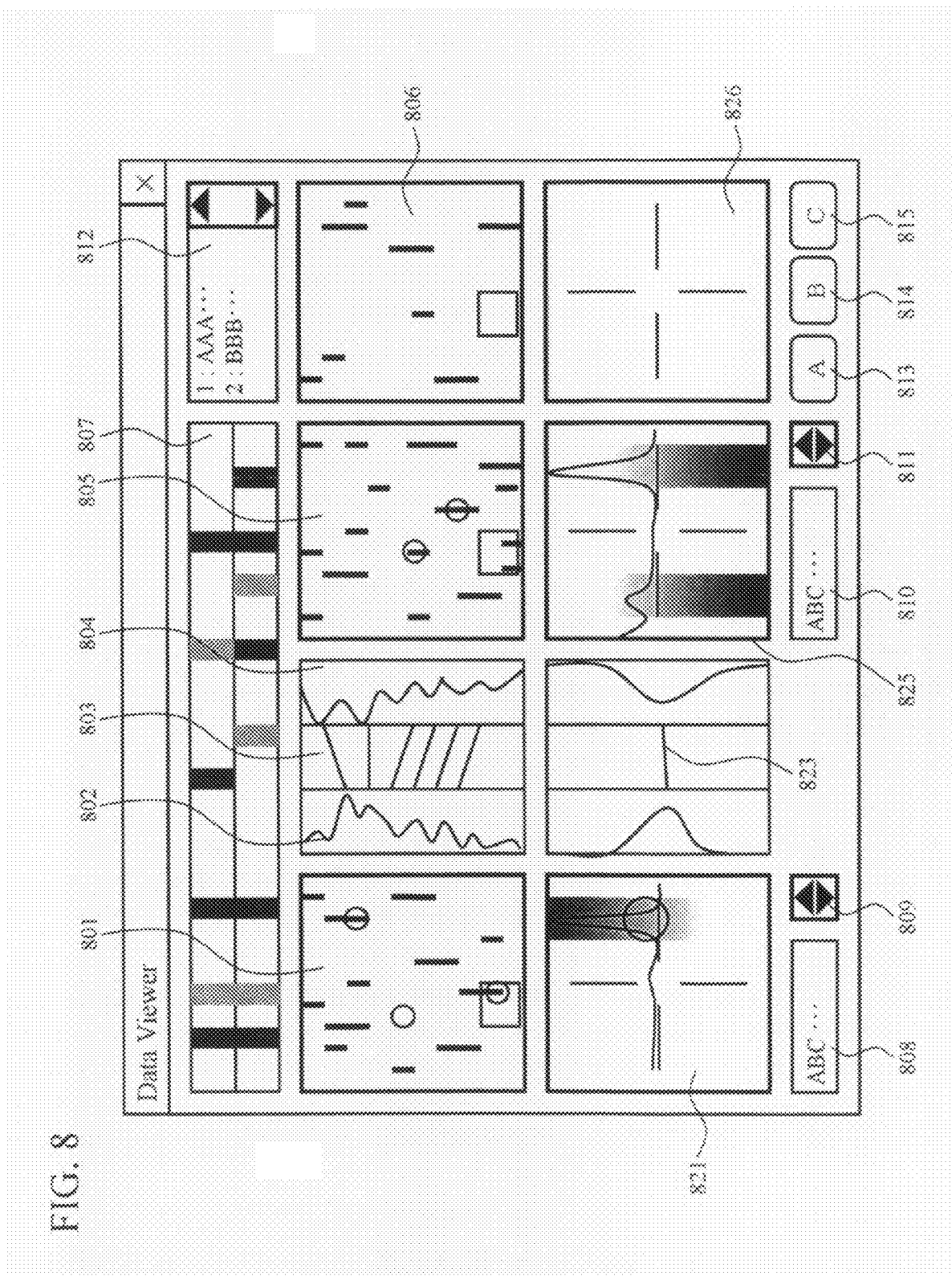
FIG. 8 is a diagram showing an example of an on-screen display.

In FIG. 8, maps 801, 805, and 806 in an upper section are capable of respectively indicating the whole of a reference sample, a sample to be corrected and comparative analysis results. In a list 812 of comparative analysis results, result values are rearranged so as to be in ascending order or in descending order and are displayed together with position information consisting of retention times and mass-to-charge ratios. Details of the comparative analysis result list 812 will be described later. In maps 821, 825, and 826 in a lower section, portions of the maps in the upper section can be displayed by being enlarged respectively.

As chromatograms 802 and 804, mass chromatograms or base peak ion chromatograms coinciding with the retention time coordinate axes of the adjacent maps are displayed by being changed according to a designation by a user. In a retention time correspondence display region 803, the correspondence relationship between the retention times in the chromatograms and maps positioned on the opposite sides are indicated by line segments. Thus, the large-region correspondence relationship is displayed in the upper section, and is partially shown in the lower section in an enlarging fashion. Reference numeral 807 denotes mass spectra corresponding to the retention time at a central position in the enlarged maps for the samples. The mass spectrum of the sample to be corrected is shown in an upper section, while the mass spectrum of the reference sample is shown in a lower section. The form of display of the chromatograms and the spectra is selected by a user from a line graph form, a histographic form reflecting the results of determination of peaks and a form based on colors or gray levels corresponding to images obtained by cutting out portions of the maps.

In an information display region 808, information including the retention time, the mass-to-charge ratio, the ion intensity and the charge number corresponding to a center in the display area of the enlarged map 821 is displayed. If a mark ○ for an identification result for example is positioned in the vicinity of the center, its contents are also displayed in this region. Buttons 809 by the side of this region are used to move the center of the visual field to the position indicated by the mark ○. The enlarged display at the position indicated by the mark ○ can be successively changed by designating one of the upper and lower triangular buttons. An information display region 810 and buttons 811 also perform the same functions.

A button A 813 is assigned to processing for obtaining retention time correction points, a button B 814 to processing for correcting retention times, and a button C 815 to establishment of correspondences between components.

Establishment of correspondences between components from correction of retention times is realized by designation through the above-described displays, buttons and list. Further, an operation to display components varying largely on the enlarged map by designating the sorted list 812 of comparative analysis results and other operations can be executed. Description will next be made of a method for displaying enlarged maps and mass spectra.

2.2 Enlarging Display Operation

In the view shown in FIG. 8, a comparatively static display for looking over the whole and a local display enabling observation of individual components are realized. A method for effectively producing local displays in particular will be described.

The following is an example of a method for producing local displays in the example of the view shown in FIG. 8.

Movement of the mouse or position designation with the mouse on large-region map 801, 805, or 806

Position designation with the mouse on local map 821, 825, or 826

Designation of line segment 803 or 823 indicating the correspondence between retention times Position designation with the mouse on a mass spectrum or a mass chromatogram Selection of an information correspondence position with information change buttons 809 or 811

Selection of list 812 of the results of computation of differences or ratios Designation of an enlarged area by dragging with the mouse or the like on one of the maps Designation of an increase or reduction in magnifying factor by means of a key input or the like (zoom-in or zoom-out operation)

Each of the maps, mass spectra and chromatograms and so on is updated in synchronization with a change in display area to maintain integrity. A user can designate whether or not all the maps are updated in synchronization with each other or each map is individually updated.

2.3 Display of Condition Setting View

Figure 9:
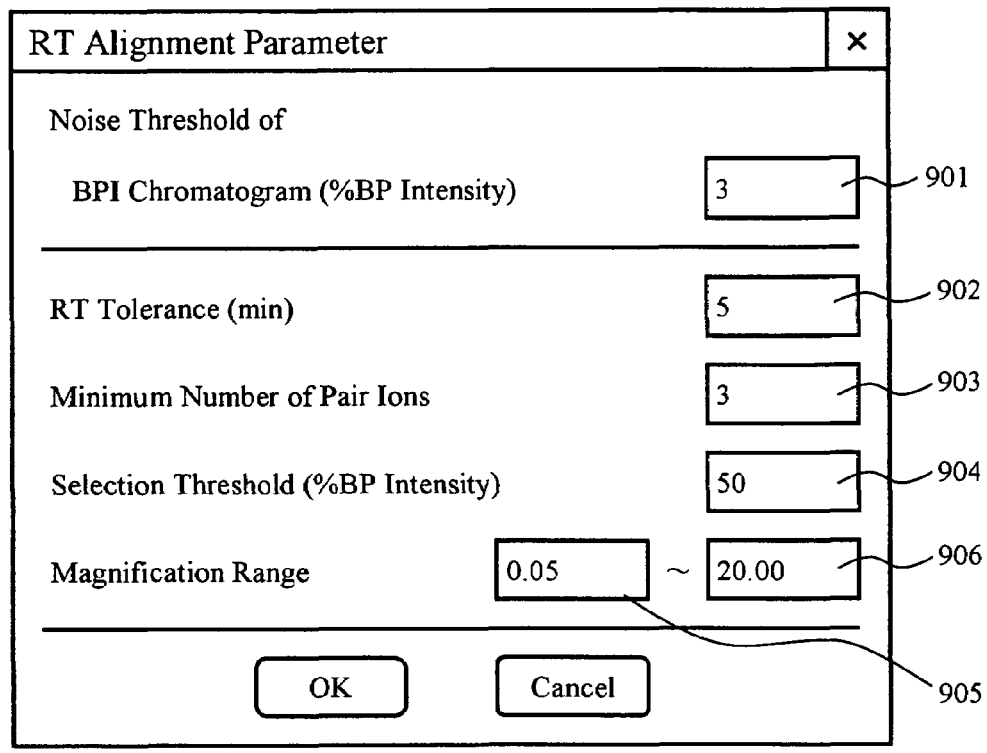
FIG. 9 is a diagram showing an example of a condition setting view for correction of retention times.

FIG. 9 shows an example of a view for setting conditions relating to correction of retention times. This view is activated from the view in FIG. 8 by depressing a function key or any other operation. The results of operations through this view are referred to, for example, in processing for obtaining correction points. The following description is made with respect to a case where a base peak ion chromatogram is used. A mass chromatogram of components to be observed may be used in place of the base peak ion chromatogram.

In the view shown in FIG. 9, a threshold 901 for peak determination on a base peak ion chromatogram, a retention time tolerance 902, a lower limit 903 of the number of coinciding pairs of ions, an ion threshold 904 referred to in comparison of mass spectra and ranges 905 and 906 of variation ratio between the samples are set. The following are examples of settings of these values:

(1) Threshold for peak determination on the base peak ion chromatogram: 3%

(2) Retention time tolerance (δt): 5 minutes (3) Lower limit of coinciding pairs of ions: 3

(4) Threshold (TH) of the relative existence amount of ions on the reference sample side: 50%

(5) Variation ratio lower limit (RL): 0.05

(6) Variation ratio upper limit (RU): 20.00

The threshold 901 for peak determination on the base peak ion chromatogram has a large influence on extraction of candidates for retention time correction points. In the case of extraction of a larger number of correction points, a smaller value of the threshold 901 is designated. In the case of extraction of a smaller number of correction points, a larger value of the threshold 901 is designated. Through the retention time tolerance 902, the maximum shift width of retention time in the entire measurement data region is designated. Increasing the value of the lower limit 903 of the number of coinciding pairs of ions means increasing the necessary number of components corresponding to each other, i.e., setting a more strict evaluation condition. The ion threshold 904 is a threshold for selecting ions used for evaluation, corresponding to the threshold 402 indicated by the broken line in FIG. 4. The variation ratio upper and lower limits 906 and 905 correspond to RU and RL in FIG. 1.

Figure 10:
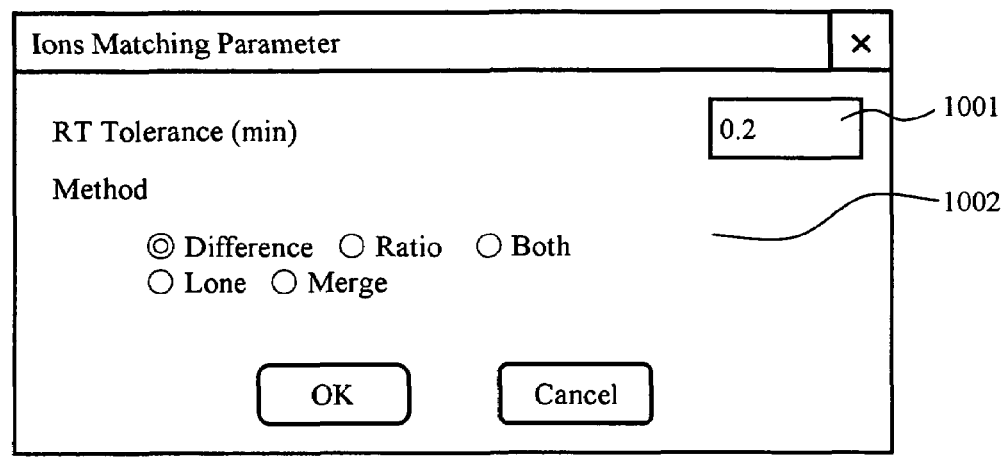
FIG. 10 is a diagram showing an example of a condition setting view for establishing correspondences between components.

FIG. 10 shows an example of a view for setting conditions used in establishing correspondences between components.

This view is also activated from the view in FIG. 8 by depressing a function key or any other operation. The following are set values in this view:

(7) Retention Time Tolerance: 0.2

(8) Computation Type: Difference

A retention time tolerance 1001 represents a tolerance with which correspondences are established between components after correction of retention times. As computation type 1002, one of displayed methods can be selected.

Computation types and display contents are shown below. Basically, samples are discriminated by colors and the magnitude of the value is expressed by the shape of the corresponding color.

Difference: The difference between components

Ratio: The ratio of components

Both: Ion intensity; for a component common to the samples, the colors of the samples are combined Lone: The ion intensity of a component existing only on one side Merge: The ion intensity of the stronger one of the samples (the sample not discriminated; single color)

2.4 Operations from Retention Time Correction to Comparative Analysis of Components The flow from correction of retention times and establishment of correspondences between components to display of components having large differences in the display view shown in FIG. 8 will be described. A state where the reference sample and the sample to be corrected and marks ○ for the corresponding identification information are displayed in the view and where the conditions shown in FIGS. 9 and 10 have already been designated is assumed. Since no correspondence relationships between retention times have been obtained, no line segments 803 indicating retention time correspondences are displayed. Also, the comparative analysis map 806 and the computation result list 812 are empty.

From such a state, the buttons A, B, and C are designated to execute processing. In the flow, the computation result list 812 is selected for checking results. Detailed description will be made of the flow.

(1) Processing by Button A

This processing corresponds to extraction of correction point candidates in step 302, evaluation of correction point candidates in step 303 and preparation of a correction point list in step 304, shown in FIG. 3. By this processing, apparent correspondences between retention times in the reference sample and the sample to be corrected are established. Line segments 803 indicating correspondences between the retention times are therefore displayed. This state corresponds to the state shown in FIG. 5(A).

A function to designate and cancel some of line segments 803 in the view in a case where there is an error in establishment of correspondences between retention times is provided. A function to add, if necessary, a new correspondence at the central position in regions displayed in an enlarged state in the two samples is also provided. Also, editing functions relating to establishment of correspondences, including a function to cancel all designations, are provided.

(2) Processing by Button B

This processing corresponds to correction of retention times in step 305 shown in FIG. 3. After the completion of this processing, contents such as those shown in FIG. 5(B) are displayed in the view shown in FIG. 8; the displays of the maps and chromatograms are updated according to the details of the correction to the retention times. Also, the line segments 803 indicating the correspondences between retention times are displayed parallel to each other.

In this state, a method including establishing finer correspondences, for example, by again executing the processing by the button A while changing the conditions shown in FIG. 9, in addition to establishing coarse correspondences, can be selected.

(3) Processing by Button C

This processing corresponds to establishment of correspondences on a component-by-component basis in step 306 shown in FIG. 3. By this processing, the comparative analysis map 806 and the computation result list 812 shown in FIG. 8 are displayed. Each map is in the state shown in FIG. 6(B), and each component is represented by one point indicating the retention time, the mass-to-charge ratio and the amount of the component.

(4) Checking Varying Components

A situation where the results of sorting after obtaining the differences between components are displayed in the list 812 when the preceding processing is completed is assumed. For example, the contents of this list include the range of components from the one that has increased by the largest amount to the one that has decreased by the largest amount. Accordingly, local maps or the like of the components that have increased are displayed by successively selecting the items from the top of the list. Similarly, if the items are successively selected from the bottom of the list, the components that have decreased can be successively checked.

As local displays, displays including maps, mass spectra and identification results are produced, thereby enabling grasp of more reliable information as to whether or not correspondences between retention times are correct and about varying components.

If, for example, such correspondence relationships are stored in a file, the correspondences between components can be statistically handled with respect to many samples.

3. Explanation of Algorithm

The processing shown in FIG. 7 and the structure of data in the processing will be described along the flow shown in FIG. 3. It is assumed here that the view shown in FIG. 8 is displayed and the contents of FIGS. 9 and 10 are designated as conditions.

3.1 Preparation of Data

In data preparation processing (703, 704), the measurement data files 701 and 702 for the reference sample and the sample to be corrected are respectively converted into the corresponding map data groups 705 and 706. This map data includes information necessary for correction of retention times and establishment of correspondences between components as well as data for displaying maps. Details of the processing will be described with reference to FIG. 11.

(1) Map Data

Figure 11:
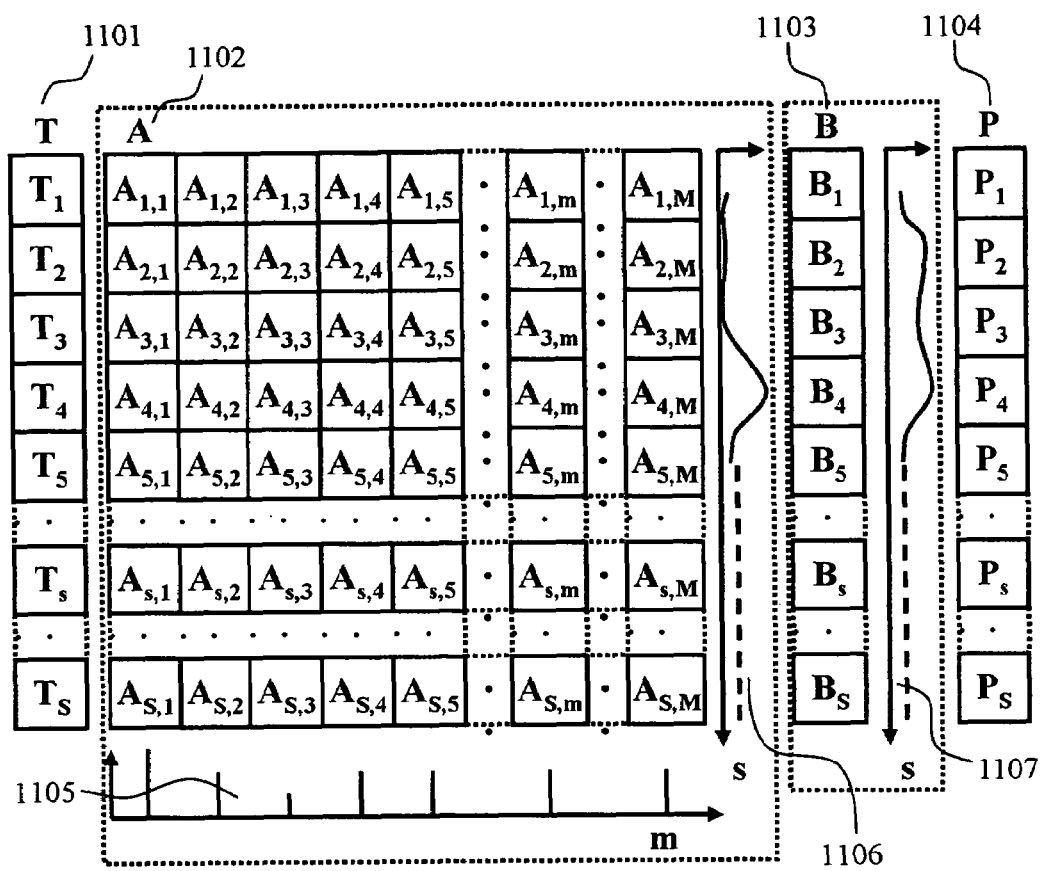
FIG. 11 is a diagram showing the data structure according to the present invention.

FIG. 11 is a schematic diagram showing map data. The meanings of symbols in FIG. 11 are as shown below.

$T_s$: Retention time of s-th mass spectrum (1101)

$A_{s,m}$: Ion intensity at mass-to-charge ratio m in s-th mass spectrum (1102)

$B_s$: Maximum ion intensity (maximum of $A_{s,1}$ to $A_{s,M}$) in s-th mass spectrum (1103)

$P_s$: Position of s-th mass spectrum in file (1104)

The meanings of the subscripts are as shown below.

m: Mass-to-charge ratio (integer: 1 to M)

M: Maximum of mass-to-charge ratio (integer)

s: Ordinal number for mass spectrum (integer: 1 to S)

S: Number of mass spectra (integer)

T represents the retention time at which a mass spectrum is observed, and A represents a two-dimensional array in which each row is a mass spectrum obtained at the same retention time and each column is a mass chromatogram showing changes in ion intensity with time at the same mass-to-charge ratio.

That is, the s-th mass spectrum is $A_{s,1}$ to $A_{s,M}$ corresponding to the retention time $T_s$ at which it is observed. An ordinary image of a mass spectrum is shown at 1105.

Changes in ion with time by which the mass-to-charge ratio m is given can be expressed as $A_{1,m}$ to $A_{S,m}$. A corresponding image is shown at 1106. In this graph, values of the ion intensity are plotted in correspondence with the ordinal numbers for the mass spectra. Such a graph or a plot of $A_{1,m}$ to $A_{S,m}$ with respect to retention times $T_1$ to $T_S$ is called mass chromatogram.

In the map data shown in FIG. 11, the mass-to-charge ratio is an integer represented by the subscript m for the array A. If the mass-to-charge ratios of the mass spectra registered in the measurement data file have digits to the right of the decimal point, processing for rounding into integers is performed in the data preparation processing. Further, if a plurality of data items correspond to one integer value, the maximum of them is prepared. If Spectra other than MS spectra, e.g., MSMS spectra exist together with mass spectra, map data is prepared only from the MS spectra.

Further, B in FIG. 11 denotes the maximum of the ion intensity in each mass spectrum. For example, the value of $B_s$ equals the maximum of $A_{s,1}$ to $A_{s,M}$. A plot of the values of $B_1$ to $B_S$ with respect to the order of mass spectra or the retention times $T_1$ to $T_S$ is called base peak ion chromatogram 1107.

In the column P, the position of each mass spectrum in the measurement data file 701 or 702 is stored. The contents of this column are used for realizing high-speed processing, for example, when an enlarged map is overwritten with the mass spectrum.

The maximum S of s is the number of mass spectra obtained in the measurement of the mass spectra, which is determined with respect to each measurement data file. A case is conceivable in which the frequency with which MS spectra are obtained varies between different measurement files. There is, therefore, a need to assume that the value of S varies between samples. That is, S in the map data on the reference sample and S' in the map data on the sample to be corrected are treated by being assumed to be different from each other. In the following, if there is a need to differentiate the notation between the samples, symbols with dashes, such as S', T', A' and B' are provided as symbols on the side of the sample to be corrected.

With respect to the maximum M of m, equality between the values M and M' is assumed by considering comparison with mass spectra in a step performed afterward.

(2) Measurement Data File

It is necessary that the measurement data files 701 and 702 be sufficient for preparing map data and capable of extracting the retention time T, the mass-to-charge ratio and the ion intensity A of MS spectra. Further, information constituting individual mass spectra is continuously registered in the measurement data file and has such a data structure as to be capable of obtaining position information P in the file for high-speed access to the head position.

3.2 Extraction of Correction Point Candidates

Extraction (707, 708) of correction point candidates will next be described. In this processing, the evaluation matrix 709 is prepared by referring to the map data groups 705 and 706 derived from the two samples. However, only a definition of the rows and columns of the matrix is given here and setting of contents is left to evaluation of correction point candidates (710).

To obtain correspondences between retention times, not evaluation of all the mass spectra but extraction of characteristic points in a discrete manner is performed. The extracted characteristic points are used for evaluation. In a method for this, peaks of base peak ion chromatograms are used.

Figure 12:
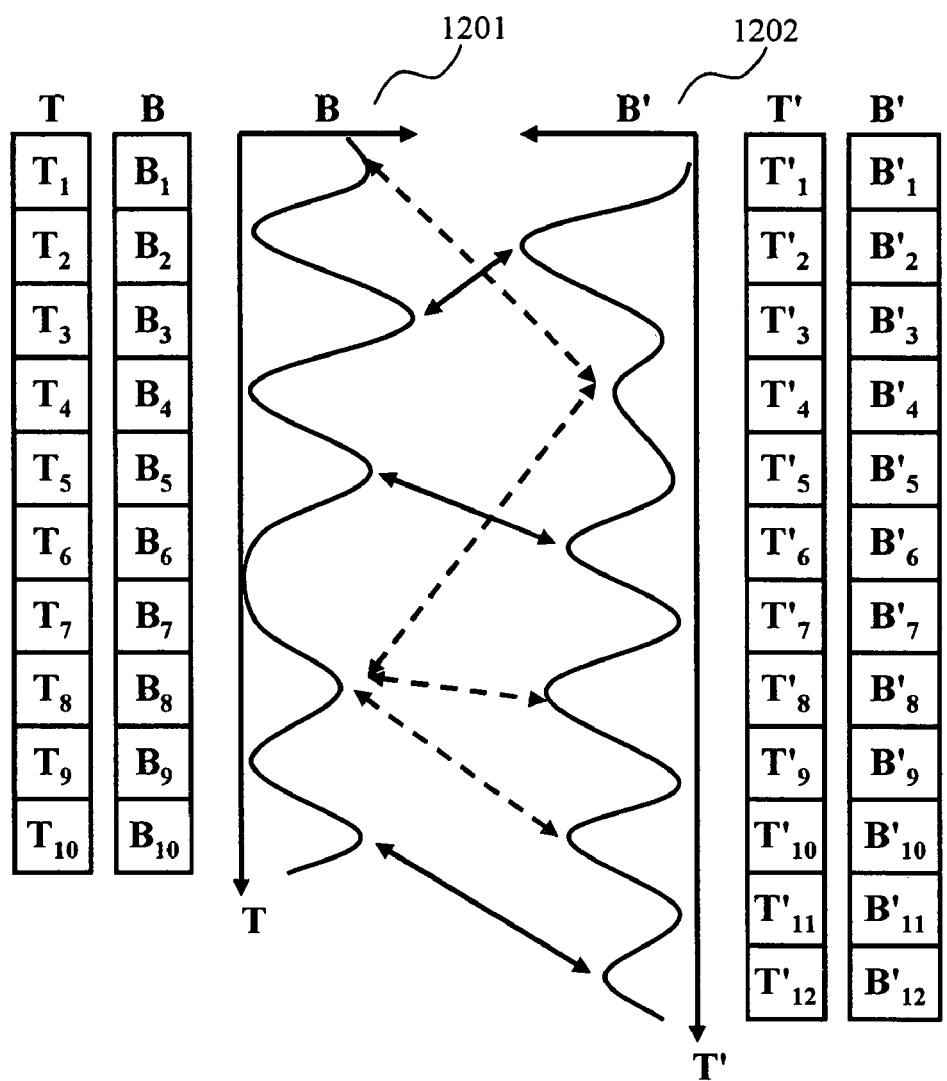
FIG. 12 is a diagram for explaining extraction and correspondence of retention time correction candidates.

Description will be made by using an example shown in FIG. 12. In FIG. 12, B, T, B' and T' are extracted from the map data on the reference sample and the sample to be corrected and the base peak ion chromatograms 1201 and 1202 of them are illustrated by being contrasted with each other. In FIG. 12, the correspondences of retention times T and T' between the samples are indicated by the arrows at the opposite ends of solid lines or broken lines indicating correspondences between peak tops, as described below in detail.

Figures 13, 14:
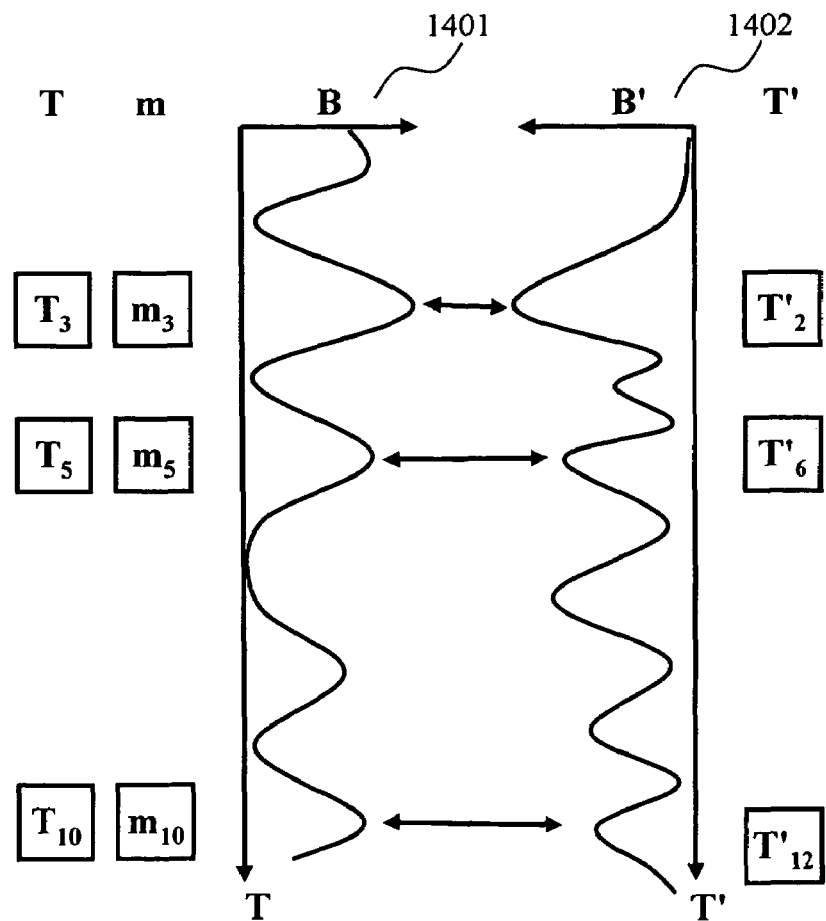
FIG. 13 is a diagram for explaining an evaluation matrix.
FIG. 14 is a diagram for explaining correction of retention times.

For example, referring to the figure, peaks are observed at $T_1$, $T_3$, $T_5$, $T_8$, $T_{10}$, $T'_2$, $T'_4$, $T'_6$, $T'_8$, $T'_{10}$, and $T'_{12}$, and can be extracted as connection point candidates. FIG. 13 shows an example of preparing an evaluation matrix from these candidates. In FIG. 13, the values of T and T' are respectively set as names of rows and columns.

B and B' indicate that at least components exhibiting those values exist. Accordingly, the components can be candidates at the time of obtaining correspondences between the samples. That is, the retention times and the mass-to-charge ratios of the components can be identified as concrete correction points. This is effective in the checking process because the components can be thereafter displayed at the time of checking correction points. That is, the correspondences between the retention times can be checked by using a local enlarged map or the like of concrete components, instead of displaying the correspondence relationship with no particular effect.

While in the example shown in FIG. 12 correspondences are established between retention times by using base peak ion chromatograms 1201 and 1202, mass chromatograms of the components to be observed may be used instead of the base peak ion chromatograms.

3.3 Evaluation of Correction Point Candidates

Evaluation of correction point candidates in step 710 shown in FIG. 7 is none other than a process for filling the evaluation matrix shown in FIG. 13. Description will be made of the evaluation matrix by using the example shown in FIGS. 12 and 13 before description of a concrete evaluation method.

(1) Evaluation Matrix

In the evaluation matrix shown in FIG. 13, the names of the rows and the columns correspond to symbols transferred from the retention times at the peaks of the base peak ion chromatograms shown in FIG. 12. Evaluation is made by a method described below as to whether there is a probability of correspondence between components with respect to all the combinations of the retention time candidates indicated in the row and columns of the evaluation matrix. The results of evaluation are set in the cells in the evaluation matrix. In the example shown in FIG. 13, mark ○ indicates a relationship in which there is a probability of correspondence between components; the nothing of mark indicates a relationship in which there is no probability; and mark x signifies that there is no probability because the difference between the retention times is equal to or larger than a certain value. Further, mark * is assigned to a one-to-one retention time relationship.

The correspondence indicated by mark ○ in the evaluation matrix is indicated by arrows at the opposite ends of a solid line or a broken line between peak tops in FIG. 12. For example, marks ○ between $T_1$ and $T'_4$, $T_3$ and $T'_2$, $T_5$ and $T'_6$, . . . in FIG. 13 correspond to the solid lines or broken lines connecting peaks of $B_1$ and $B'_4$, $B_3$ and $B'_2$, $B_5$ and $B'_6$, . . . in FIG. 12. Each solid line indicates a one-to-one relationship, and the broken lines indicate other cases.

In a case where a plurality of correspondences are suggested with respect to one retention time as indicated by the broken lines in FIG. 12, the retention time is not suitable as a correction point. Only the relationships shown by connecting peaks by the solid line, i.e., the relationships given mark * in the evaluation matrix, are used in preparation of a correction point list (711) subsequently performed. That is, in the example shown in FIGS. 12 and 13, only the correspondences between $T_3$ and $T'_2$, $T_5$ and $T'_6$, and $T_{10}$ and $T'_{12}$ are adopted.

(2) Evaluation of Mass Spectra

Evaluation of individual correction point candidates, i.e., processing for assigning mark ○ in the evaluation matrix shown in FIG. 13, is performed. This evaluation corresponds to comparison between mass spectra $A_{3,1}$ to $A_{3,M}$ and $A'_{2,1}$ to $A'_{2,M'}$ (M=M') corresponding to the retention times to be compared (e.g., $T_3$ and $T'_2$).

When correspondences are obtained, correction candidates are discretely extracted by applying the threshold 901 shown in FIG. 9, and determination is made under the conditions from 902 to 906 in evaluation of mass spectra. In this determination, with respect to all the ions satisfying the condition shown by equation (7) in the mass spectra obtained from the two samples, coincidence is recognized only when equation (8) is satisfied.

$$I_m \geq I_{max} \times TH/100 \quad (7)$$

$$I_m \times RU \geq I'_m \text{ and } I_m \times RL \leq I'_m \quad (8)$$

$I_m$: Ion intensity observed at mass m in reference sample
$I'_m$: Ion intensity observed at mass m in sample to be corrected
$I_{max}$: Maximum of ion intensity on the reference sample side
TH: Threshold (904)
RL: Variation ratio lower limit (905)
RU: Variation ratio upper limit (906)

In the example shown in FIG. 9, with respect to ions at 50% of the maximum of the relative existence amount in the mass spectrum in the reference sample, noncoincidence is determined when the compared sample has a variation width out of the range from 0.05 to 20.

However, when the difference between the retention times before correction is larger than the designated value of the retention time tolerance 902, this evaluation is not performed and no probability of correspondence is recognized (corresponding to mark x in the evaluation matrix). Also when the number of ions satisfying this condition is smaller than the value designated as the lower limit 903 of the number of coinciding pairs of ions, coincidence is not recognized (corresponding to a blank in the evaluation matrix).

RU and RL referred to here are used in the same definition as those of RU and RL in the above-described equations (1) and (2). δm in equations (3) and (4) corresponds to 0, and δt in equations (5) and (6) corresponds to the retention time tolerance 902.

3.4 Preparation of Correction Point List

When points given mark * are obtained in the evaluation matrix, processing (711) for preparing the correction point list 712 for concretely correcting retention times is executed.

The concept of the correction point list will be described with reference to FIG. 14 showing the correspondence between base peak ion chromatograms after correction. In FIG. 14, T and T' coincide with the example indicated by mark * in the example shown in FIG. 13. The value of m is the mass-to-charge ratio obtained from the mass spectrum observed at the corresponding retention time T. This value is selected from the mass-to-charge ratios of ions observed in common in the mass spectra compared with each other.

For example, the mass-to-charge ratio at which the maximum of the ion intensity in the mass spectrum on the reference sample side is exhibited can be adopted as m. At this point in time, correspondence with a particular component is established as a retention time correction point.

The retention time of the component obtained here does not necessarily coincide completely with the peak position of the base peak ion chromatogram. Then a search is made for the peak of the mass chromatogram corresponding to the mass-to-charge ratio of the component and retention time correction points are determined.

If the mass spectrum is observed at the retention time ($T_s$), m at which its maximum intensity is exhibited is obtained, and the retention time of the peak containing $T_s$ in the mass chromatogram ($A_{1,m}$ to $A_{S,m}$) corresponding to m is set as the optimum value of $T_s$. Similarly, also with respect to $T'_{s'}$ on the side of the sample to be corrected, the peak corresponding to $T'_{s'}$ is obtained from the mass chromatogram ($A'_{1,m}$ to $A'_{S,m}$) and $T'_{s'}$ is updated. By performing such processing, a pair of ions (m observed at $T_s$ and m observed at $T'_{s'}$) used for correction of the retention time are selected and added to the correction point list. Such processing is executed with respect to all the items given mark * in the evaluation matrix to determine the correction point list.

3.5 Correction of Retention Times

Correction of retention times in step 713 shown in FIG. 7 is a process for reflecting in the map data on the sample to be corrected the correspondence relationships of the correction points registered in the correction point list 712. This process is none other than a process for changing the retention times T' 1101 shown in FIG. 11.

Description will be made of the example shown in FIG. 14. This example shows base peak ion chromatograms after correction. In this example, the peak observed at $T'_2$ in the sample to be corrected is to be corrected to $T_3$. Similarly, since $T'_6$ corresponds to $T_5$, and $T'_{12}$ to $T_{10}$, each T' is changed to the value of T of the reference sample. Each of retention times with no correspondence with the standard sample is interpolated between preceding and subsequent corresponding correction points by assuming its proportionality. Extrapolation is made by assuming continuation of an error in the closest correction point list.

The retention times are corrected in this way to update the entire region of the retention time T' in the map data 706 on the sample to be corrected.

3.6 Establishment of Correspondences Between Components

In processing for establishing correspondences between components (714), processing for obtaining representative points of individual components by referring to the maps 705 and 706 after correction of the retention times derived from the samples and processing for executing designated computation between the samples on a component-by-component basis and registering the results of computation in the computation result list (812 in FIG. 8) are performed. Map display of the computation results will be described below in detail.

(1) Extraction of Component Representatives

Also in the measurement data on the samples corrected in a large-region manner, each of individual components is observed as a temporary change in an ion group including an isotope. Obtaining correspondences between the individual components requires extracting representative points therefrom as the values of the retention times and the mass-to-charge ratios. The results of this extraction can be expressed as shown in FIG. 6(B).

To obtain representatives of the components, a method may be used in which peak tops about all the mass chromatograms for example are left to be set as representative candidates, and in which, if two representative candidates exist adjacent to each other at one retention time, one of the representative candidates higher in intensity is selected.

The values of the ion intensities of representative points may be replaced by applying, for example, the heights of the left representative points and the volumes of the points eliminated by extraction of the representatives of the components.

(2) Establishment of Correspondences Between Components

Correspondences of the representative points of the components thus extracted are established between the reference sample and the sample to be corrected. More specifically, map data 715 on the results of establishment of correspondences between the components is prepared and initialized. At this time, the size of each array is set equal to that of the map data 705 on the reference sample. Also the retention times are assumed to be the same and are copied. That is, in the reference sample map data 705 and the map data 715 as the results of establishment of correspondences between the components, the same positions in arrays A correspond to the same retention time and mass-to-charge ratio.

If, with respect to each of the representative points in the map 706 of the sample to be corrected, a component having the retention time with an error within the tolerance 1001 designated in FIG. 10 and having the same mass-to-charge ratio exists in the reference sample, it is regarded as identical and registered in the map data 715. If no match exists, the representative point is considered to exist only in the sample to be corrected and is registered at a position of the closest retention time and mass-to-charge ratio. The map data 715 prepared as the results of establishment of correspondences between the components can be easily compared with the map data on the reference sample.

(3) Computation and Display of Comparative Analysis Map

While the map 801 of the reference sample and the map 805 of the sample to be corrected have the ion intensity replaced with color information, the comparative analysis map 806 has display color of each component determined by referring to the map data 705 on the reference sample and the map data 715 as the results of establishment of correspondences between the components.

In an example shown in FIG. 15, association of the ion intensity of each sample, a computation result, and three primary colors constituting a display color is shown. In this example, computed values or the like are directly designated in the three primary colors. In actuality, an upper limit is specified, for example, by multiplying the value by a suitable multiplying factor. That is, a display in white is produced if each of the three primary colors has the upper limit value, and a display in black is produced if each of the three primary colors is 0.

Also, in this example, an ion strongly observed on the reference sample size is associated with red, while an ion strongly observed on the side of the sample to be corrected is associated with green. The same association is also established in displaying the results of computation of the difference or ratio. Description will be made in more detail below with respect to each computation type.

In the case of computation type "Difference", the ion intensity of the reference sample is subtracted from the ion intensity of the sample to be corrected to obtain a computed value. When the computed value is negative, the absolute value of the computed value is set in red. When the computed value is positive, the absolute value of the computed value is set in green. As a result, discrimination between the samples and recognition of a change in amount are made possible by means of colors and the depth of colors. (Nos. 1 and 2)

In the case of computation type "Ratio", the ion intensity of the sample to be corrected is divided by the ion intensity of the reference sample. However, if the value of the sample to be corrected is smaller, the reciprocal of this division is computed and the result is multiplied by (−1) to be obtained as a negative value. Further, when the computed value is negative, the absolute value of the computed value is set in red. When the computed value is positive, the absolute value of the computed value is set in green. As a result, discrimination between the samples and recognition of the ratio are made possible by means of colors and the depth of colors. Since in the result list 812 the negative numeric value indicates a decrease, a discrimination between the two cases is facilitated. (Nos. 3 and 4)

In the case of "Both", the ion intensities derived from the two samples are set in red and green. (Nos. 5 and 6)

In the case of "Lone", a similar indication is also made. However, the indication is limited to cases where there are no components corresponding to each other. That is, in a case where components in the two samples correspond to each other as in the example No. 9, all the values of the three colors for display are set to 0. (Nos. 7, 8, and 9)

In the case of "Merge", the stronger one of the values of two samples is set in red. In this case, however, red is determined for convenience sake, and does not signify the reference sample. (Nos. 10 and 11)

The comparative analysis map 806 is prepared in this way. In the contents of the map, varying items in the samples can be looked over. Further, after sorting and registration in the computation result list 812, characteristic components varying largely can be explicitly shown. Further, operations including an operation to produce an enlarged display of the positions of such components are made possible.

It is also effective to indicate a sequence of strongly observed items in the computation result list, for example, by using the stronger one of the ion intensities of the samples as a computed value other than the difference or ratio value.

The embodiment of the present invention has been described to explain concrete means for correcting retention times, establishing correspondences between components and performing comparative analysis on varying components.

The advantages of the present invention are summarized below.

1. About Method of Establishing Correspondences Between Components

The method of the present invention has a reduced dependence on the retention time at the time of establishing correspondences between components. Because of this characteristic, the method provides increased choices including a choice to measure MSMS spectra at the time of measurement. An example of the effects will be described below.

(1) Acquisition of Component Identification Information

In mass spectrometry, MSMS spectra or the like can be simultaneously obtained in order to obtain information about the structure of each individual component. In some case, MSMS spectra enable identification of observed components. That is, the method of the present invention enables both identification of components and acquisition of quantitative knowledge through one round of measurement.

(2) Comparison of Different Measurement Modes

Measurement results obtained by continuously obtaining only MS spectra and results obtained by also obtaining MSMS spectra simultaneously with the MS spectra can be contrasted with each other. In the former results, trace components can also be captured and an improvement in quantitativeness is achieved. In the latter results, component structure information or the like can be provided. Quantitative knowledge and qualitative knowledge can be unified from measurement results obtained by different methods.

(3) Study of Experimental Conditions

With respect to comparison between retention times, the method of the present invention is probable to be applicable to a case where the amount of retention time shift is large. That is, full use of the method can be made even at a stage of studying conditions for experiments including separation.

Further, effects described below can be expected because of the adopted algorithm.

(4) Application of Low-Priced Computation Facilities

The method of the present invention uses a comparatively small amount of computation and does not require a large storage capacity. Therefore correction of retention times, establishment of correspondence between components, checking of varying components, etc., can be realized without using a computation processing environment such as an analysis server or a PC cluster.

(5) Realization of High-Speed Processing

Since processing can be finished in a short time, it is possible to examine results by changing conditions according to characteristics of samples to be compared. For example, conditions dependent on characteristics of samples, such as a peak determination threshold and an assumed range of variation of components, can be easily optimized.

(6) Coexistence with Other Functions

Since processing can be finished in a comparatively short time without imposing a large load on a computer, correction of retention times and establishment of correspondences between components can be realized through a form of dialog with a user. Incorporation of processing according to the method of the present invention, for example, in a method of checking establishment of correspondences between components as described below or a like method is enabled.

2. About Method of Checking Establishment of Correspondences Between Components

A process of visually expressing and efficiently checking differences between retention times in different materials and information on corresponding components is very important. According to the present invention, a method of making a large-region check on the results of chromatography mass spectrometry on at least two samples and a method of efficiently checking the correspondences between individual components existing locally are provided. The effects of the method of making a large-region check will first be described.

(1) Display of Entire Measurement Data

All of a plurality of measurement data items to be compared can be displayed as a map. By looking over retention times and the mass-to-charge ratios and intensities of observed ions, changes in the total ion intensity due to sampling and preprocessing, chemical noise, the state of a component of an excessively large content, etc., can be visually checked. In this way, information important in determination as to the quality of experiment, the condition of an apparatus can be provided.

Also, positions at which MSMS spectra were obtained and positions at which identification information items exist may be marked on a map and relating concrete contents may be displayed. This contributes to evaluation of the results of identification processing or the like.

(2) Grasp of Correspondence Relationship Between Retention Times

The state of correspondences between retention times can be looked over through the entire measurement region. In the event of an abnormality in establishment of correspondences between retention times, a probability of a trouble in a separating unit or the like can be presented.

(3) Grasp of Correspondence Relationship on Component-by-Component Basis

After execution of correction of retention times, the results of computation of the amounts of individual components of different samples can be displayed as a map. In this way, a component having a large quantitative variation difference, a component having a high variation ratio, a component observed only in one of the two samples and other components can be extracted and explicitly shown on a map. Further, a list of such computation results may be displayed to facilitate determination of characteristic components.

Also, a local checking operation achieved by substantiating the correspondences of individual components between samples can be efficiently performed. Such local checking operations have effects described below.

(4) Local Enlargement

Items shown in a large-region display can be checked in more detail. A map display in particular enables comparison of vicinal states between samples in terms of retention time and mass-to-charge ratio. This is an important decisive factor in establishment of correspondences between components.

(5) Display of Auxiliary Information Derived from Mass Spectra

Information on different samples derived from mass spectra of corresponding components can be displayed simultaneously with a map Mass-to-charge ratio, charge number of ions, mass in the case of single-charge Whether or not MSMS spectra have been obtained Actual mass spectra (waveform information)

Display of identification results

Display of these sorts of information is also important in evaluating the correspondences between components. It is assumed that the contents of a display of identification results or the like are prepared in an external system and imported.

Such a local display is realized by designating, for example, the above-described computation result list, the positions on a map showing the entire region and the correspondence relationship of retention times between samples. Designation of these items can be performed by a simple operation such as moving a mouse or designating a list. The display can be produced simultaneously with the designation. That is, observing components of large variations or the like and successively checking mass spectra and identification results are easily realized.

Through a large-region display, the results of measurement of different samples and the state of establishment of correspondences between components can be looked over, and the correspondence between individual components can be easily checked from the important one. This leads to saving of a large amount of labor and time.

3. Other Effects

The effects in a case where a mixture including a sample to be compared is provided as a reference sample and where the sample before mixing is analyzed as a sample to be corrected are shown below.

(1) Increasing Analyzable Samples

Comparison is enabled even between samples having different components.

(2) Improvement in Accuracy of Establishment of Correspondences Between Components Ideally, all the components of the sample to be corrected are also observed in the reference sample. Therefore, corresponding ions are increased; a contribution to the provision of sufficient retention time correction points is made; and the correction accuracy is improved.

(3) Comparison Between Three or More Samples

The concept of comparison between two samples can be directly extended to comparison among three or more samples. That is, setting of a reference sample covering the components of other samples is enabled, so that the above-described effects can be applied to comparison among a plurality of samples.

What is claimed is:

1. A chromatography-mass spectrometry method comprising:
    comparing at least two samples with respect to the ion intensity corresponding to retention times and mass-to-charge ratios obtained by chromatography-mass spectrometry on the two samples; and
    establishing, in ion groups observed as mass spectra, a correspondence between the retention times at which the same component is observed, by determining coincidence between the mass-to-charge ratios and determining that the relative existence amounts fall within a designated variation.

2. The chromatography-mass spectrometry method according to claim 1, wherein retention time correction points are discretely extracted by using peaks of mass chromatograms of components to be observed or chromatograms formed of the maximums of the individual mass spectra;
    coincidence between component groups is determined on the basis of the mass-to-charge ratios at the peak positions and a range of variation of the ion intensity; and
    ions to be used for correction of the retention times are selected.

3. The chromatography-mass spectrometry method according to claim 2, wherein the results of chromatography-mass spectrometry of the two samples are displayed on a map by indicating the retention times on a common coordinate axis, and by indicating the ion intensity by colors or shades with respect to the coordinate axes representing the retention time and the mass-to-charge ratio; mass chromatograms of the components to be observed in the samples or chromatograms formed of the maximums of the individual mass spectra are displayed side by side; and the retention times at which the components correspond to each other are displayed in a state of being connected by line segments.

4. The chromatography-mass spectrometry method according to claim 3, wherein, with respect to the retention times and the mass-to-charge ratios corresponding to each other between the two samples, values of differences or ratios in ion intensity, ion intensities existing in only one of the two samples or the ion intensities of the two samples are indicated as a gray-level map by being color-coded according to the values or the samples from which the ion intensities are derived.

5. The chromatography-mass spectrometry method according to claim 3, wherein, if information such as the results of identification corresponding to the retention times and the mass-to-charge ratios exists, marks are displayed at the corresponding positions on the map to explicitly show the existence of the information.

6. The chromatography-mass spectrometry method according to claim 3, wherein when designation of a position or selection of a component is performed with a mouse, a map and a chromatogram in which a portion of the map in the vicinity of the corresponding retention time and mass-to-charge ratio is enlarged and information about an observed ion are displayed.

7. The chromatography-mass spectrometry method according to claim 6, wherein the mass spectrum corresponding to the retention time is displayed so that the enlarged map is overwritten with the mass spectrum.

8. The chromatography-mass spectrometry method according to claim 3, wherein individual components are displayed by being each represented by one point for the retention time and the mass-to-charge ratio.

9. A chromatography-mass spectrometry method comprising the steps of:
    preparing, on the basis of data representing the relationship between retention times and mass spectra obtained as a result of chromatography mass spectrometry of a first sample, a first chromatogram formed of a mass chromatogram of components to be observed or a base peak ion chromatogram in which the maximums of the ion intensity in the mass spectra are plotted with respect to the retention times;
    preparing, on the basis of second data representing the relationship between retention times and mass spectra obtained as a result of chromatography mass spectrometry of a second sample, a second chromatogram formed of a mass chromatogram of the components to be observed or a base peak ion chromatogram in which the maximums of the ion intensity in the mass spectra are plotted with respect to the retention times;
    establishing correspondences between peaks of the first chromatogram and peaks of the second chromatogram by comparing the mass spectra of the peaks of the first chromatogram and the mass spectra of the peaks of the second chromatogram; and
    correcting the retention times of the mass spectra of the second sample so that the retention times of the peaks of the first and second chromatograms, between which correspondences are established in the preceding step, are equal to each other.

10. The chromatography-mass spectrometry method according to claim 9, wherein when one of the peaks of the second chromatogram having a difference in retention time from the peaks of the first chromatogram equal to or shorter than a time period set in advance is observed, and when, in the mass spectrum thereof, the intensity of an ion having an ion intensity equal to or higher than a threshold set in advance in the mass spectrum of one of the peaks of the first chromatogram is within a variation set in advance with respect to the ion intensity equal to or higher than the threshold, a correspondence is established between the two peaks.

11. The chromatography-mass spectrometry method according to claim 10, wherein a state where the number of ions having an ion intensity equal to or higher than the threshold set in advance is larger than a number set in advance is set as a condition for establishing a correspondence between the two peaks.

12. The chromatography-mass spectrometry method according to claim 9, wherein a retention time between adjacent two of the retention times corrected on the basis of the peaks is corrected by proportional interpolation between the two retention times.

13. The chromatography-mass spectrometry method according to claim 1 or 9, wherein a mixture in which the samples to be compared are mixed is provided as the first sample, and one of the samples before mixing is provided as the second sample.

14. A chromatography-mass spectrometry apparatus comprising:
a data processing section in which data indicating the relationship between retention times and mass spectra of an input first sample and data indicating the relationship between retention times and mass spectra of an input second sample are compared to correct the retention times of the data derived from the second sample, and
a display section,
wherein the data processing section prepares, from the data indicating the relationship between the retention times and the mass spectra, a chromatogram formed of a mass chromatogram of components to be observed or a base peak ion chromatogram in which the maximums of the ion intensity in the mass spectra are plotted with respect to the retention time, establishes correspondences between peaks of the chromatogram derived from the first sample and peaks of the chromatogram derived from the second sample by comparing mass spectra of the peaks of the chromatogram derived from the first sample and mass spectra of the peaks of the chromatogram derived from the second sample, and corrects the retention times of the mass spectra of the second sample so that the retention times of the peaks of the chromatogram derived from the first sample and the retention times of the peaks of the chromatogram derived from the second sample, between which correspondences are established, are equal to each other, and
wherein the display section displays, on a map, data derived from the first sample and data derived from the second sample by indicating the retention times on a common coordinate axis, and by indicating the ion intensity by colors or shades with respect to the coordinate axes representing the retention time and the mass-to-charge ratio, displays side by side the chromatogram derived from the first sample and the chromatogram derived from the second sample by connecting the corresponding peaks by line segments.

15. The chromatography-mass spectrometry apparatus according to claim 14, wherein when one of the peaks of the chromatogram derived from the second sample, which peak has a difference in retention time from the peaks of the chromatogram derived from the first chromatogram, which difference is equal to or shorter than a time period set in advance, is observed, and when, in the mass spectrum thereof, the intensity of an ion having an ion intensity equal to or higher than a threshold set in advance in the mass spectrum of one of the peaks of the chromatogram derived from the first chromatogram is within a variation set in advance with respect to the ion intensity equal to or higher than the threshold, a correspondence is established between the two peaks.

16. The chromatography-mass spectrometry apparatus according to claim 14, wherein, with respect to the retention times and the mass-to-charge ratios corresponding to each other between the first sample and the second sample, values of differences or ratios in ion intensity, ion intensities existing in only one of the two samples or the ion intensities of the two samples are indicated as a gray-level map by being color-coded according to the values or the samples from which the ion intensities are derived.

17. The chromatography-mass spectrometry apparatus according to claim 16, wherein components differing in ion intensity between the first sample and the second sample are displayed in ascending order or descending order according to the differences in ion intensity.

18. The chromatography-mass spectrometry apparatus according to claim 14, wherein when designation of a position or selection of a component is performed with a mouse, a map and a chromatogram in which a portion of the map in the vicinity of the corresponding retention time and mass-to-charge ratio is enlarged and information about an observed ion are displayed.

19. The chromatography-mass spectrometry apparatus according to claim 18, wherein the mass spectrum corresponding to the retention time is displayed so that the enlarged map is overwritten with the mass spectrum.

20. The chromatography-mass spectrometry apparatus according to claim 14, wherein individual components are displayed by being each represented by one point for the retention time and the mass-to-charge ratio.

21. The chromatography-mass spectrometry apparatus according to claim 14, wherein a mixture in which the samples to be compared are mixed is provided as the first sample, and one of the samples before mixing is provided as the second sample.

* * * * *